United States Patent

Asada et al.

[11] Patent Number: 5,953,773
[45] Date of Patent: Sep. 21, 1999

[54] SURFACE WAVE DISTRIBUTED ACTUATOR SYSTEMS

[75] Inventors: Haruhiko H. Asada, Concord, Mass.; Joseph Spano, Lodi, Calif.; William H. Finger, Huntington Station, N.Y.

[73] Assignee: Massachusetts Institute of Technology, Cambridge, Mass.

[21] Appl. No.: 09/035,235

[22] Filed: Mar. 5, 1998

Related U.S. Application Data

[60] Provisional application No. 60/039,981, Mar. 5, 1997, and provisional application No. 60/053,889, Jul. 28, 1997.

[51] Int. Cl.$^6$ ........................................................ A61G 7/10
[52] U.S. Cl. .......................... 5/81.1 R; 5/81.1 HS; 5/674; 5/693
[58] Field of Search ............................. 5/81.1 R, 81.1 L, 5/81.1 HS, 612, 693, 697, 674, 715, 915, 933, 935, 937; 601/48, 49, 53, 54, 57, 90, 91, 92, 93

[56] References Cited

U.S. PATENT DOCUMENTS

| | | | |
|---|---|---|---|
| 378,220 | 2/1888 | Staples et al. | 5/81.1 C |
| 1,772,310 | 8/1930 | Hart | 5/933 X |
| 4,136,409 | 1/1979 | Ishida | 5/91 |
| 4,227,608 | 10/1980 | Alfthan et al. | 198/630 |
| 4,542,547 | 9/1985 | Sato | 5/715 X |
| 4,639,959 | 2/1987 | Roca | 5/674 |
| 4,667,358 | 5/1987 | Penterman | 5/674 |
| 4,982,465 | 1/1991 | Nagata et al. | 5/709 X |
| 4,999,861 | 3/1991 | Huang | 5/60 |
| 5,375,273 | 12/1994 | Bodine, Jr. et al. | 5/715 X |

FOREIGN PATENT DOCUMENTS

| 2 114 522 | 8/1983 | United Kingdom . |
|---|---|---|
| WO 95/21600 | 8/1995 | WIPO . |

*Primary Examiner*—Michael F. Trettel
*Attorney, Agent, or Firm*—Bromberg & Sunstein LLP

[57] ABSTRACT

An apparatus for positioning a human subject on a surface and for transferring a subject from one surface to another. The subject is situated on the top surface of a fluid enclosure and an actuator mechanism causes local deformations of the top surface in such a manner as to create traveling waves whereby a force tangential to the top surface is exerted on the subject for moving the subject with respect to the surface. The actuator mechanism may be a motor driver and may be a plurality of linear actuators configured so as to cause local deformations of the top surface in a direction having a vertical and/or horizontal component. The linear actuators may be shape memory fibers.

16 Claims, 12 Drawing Sheets

SURFACE WAVE DISTRIBUTED ACTUATOR SYSTEMS

The present application claims priority from U.S. provisional applications 60/039,981, filed Mar. 5, 1997, and U.S. provisional application 60/053,889, filed Jul. 28, 1997, which are herein incorporated by reference.

FIELD OF THE INVENTION

This invention relates to active surfaces for controlling the position and posture of a human body, and, more particularly, to surfaces activated by shape memory materials.

BACKGROUND ART

Transferring a disabled person from a wheelchair to various fixtures or means of conveyance is an extremely laborious physical job that an average person may perform only with difficulty, if at all. During the course of a day, a patient may need to be transferred to a bed, a toilet, a bath, a car, or to various pieces of medical equipment, and, additionally, may require positioning or repositioning once situated on a given fixture or conveyance. The majority of the elderly currently residing in nursing homes or hospitals have been admitted primarily because they can no longer function in their home environment while permanently bedridden. A variety of devices for lifting bedridden persons have been developed and deployed at both homes and hospitals. Many of these devices, however, are awkward, uncomfortable, and often frightening for the elderly. They require direct, physical effort on the part of the caretaker to manually operate, and during transfer, the body may be airborne, tending to swing and rotate, and may cause both discomfort and embarrassment for the patient.

Other examples of direct physical assistance which caregivers may provide include transfer of the patient from one surface to another, positioning of the patient of a surface, changing the clothing and bed sheets of a patient. For example, to prevent bedsores, a caregiver must change the posture of the patient every 3 to 4 hours to maintain blood flow that may be impeded in certain flesh regions for a long period of time. In addition, the posture must be changed to provide stimuli to elderly people with severely debilitated physical activity levels. These tasks which include physical interactions with the bedridden are currently performed by human caregivers. As the population of elderly persons grows, it is desirable that the costly, labor-intensive services described above be provided by the fixture itself.

A human body has numerous degrees of freedom. To successfully transfer a bedridden person to a chair and alter the patient's posture in a natural way by mechanical assistance requires many degrees of freedom. It is difficult to build such equipment using traditional actuators. New technologies are needed to effectively interact with human bodies and perform diverse tasks safely and reliably.

SUMMARY OF THE INVENTION

In accordance with a preferred embodiment of the present invention, there is provided an apparatus for supporting a human subject. The support apparatus has a fluid enclosure containing a fluid and having a top surface, as well as an actuator mechanism for causing local deformations of the top surface of the fluid enclosure in such a manner as to create traveling waves whereby a force tangential to the top surface is exerted on the subject. The actuator mechanism may include a motor driver coupled to the top surface of the fluid enclosure and may include a plurality of linear actuators configured so as to cause local deformations of the top surface in a direction having a vertical component.

In accordance with various alternate embodiments of the present invention, the apparatus may be a bed, a chair, a medical examining table, or a car seat. The plurality of linear actuators may include shape memory fibers, and the plurality of linear actuators may be configured to cause lateral deformations of the top surface of the fluid enclosure. Additionally, the plurality of fiber actuators configured to cause lateral deformations of the top surface of the fluid enclosure bag may be woven into the top surface.

In accordance with another aspect of the present invention, there is provided a method for transferring a human subject from a first surface to a second surface, the method comprising the steps of positioning the first and second surfaces in substantial adjacency and at substantially equal height, causing local deformations of the first surface in a direction having a vertical component, and coordinating the local deformations of the first surface in such a manner as to create traveling waves whereby a force tangential to the first surface is exerted on the subject thereby urging the subject onto the second surface. In accordance with alternate embodiments of the present invention, at least one of the first and second surfaces may be a chair.

In accordance with yet another aspect of the present invention, there is provided a method for transferring a human subject from a surface to a bathtub having a bathtub hoist seat, the method having the steps of docking the surface in substantial adjacency and at substantially equal height to the bathtub hoist seat, causing local deformations of the surface in a direction having a vertical component, coordinating the local deformations of the surface in such a manner as to create traveling waves whereby a force tangential to the surface is exerted on the subject thereby urging the subject onto the bathtub hoist seat, and lowering the subject into the bathtub by means of the bathtub hoist seat. A method is also provided for repositioning apparel of a human subject prone or recumbent on a surface, wherein the method has the steps of causing local deformations of the surface in a direction having a vertical component such as to support the subject other than through an unsupported portion of the apparel and other than through a groove wherein the surface does not contact the subject, and tucking the portion of the apparel away from the subject into the groove. Finally, a method is provided for positioning a human subject on a surface, the method having the steps of causing local deformations of the surface in a direction having a vertical component such as to support the subject in specified locations, and coordinating the local deformations of the surface in such a manner as to create traveling waves whereby a force tangential to the surface is exerted on the subject thereby urging the subject into a specified position.

As taught in further detail in the description below, distributed actuators generate surface waves that propagate on the top surface of the fluid enclosure. This propagation acts as the physical transport mechanism that manipulates the human body lying on the surface. Without additional equipment, the bedridden can be moved by the surface itself. Moreover, wave patterns can be changed so that different parts of the human body can be moved separately. For bedsore prevention, one dimensional waves of low frequency would be generated so that the human body would be supported at alternating contact areas. By generating various wave patterns, a broad spectrum of stimuli can be provided to the human body.

An array of fiber actuators which may be made of NiTi shape-memory alloy (SMA) are woven into the top surface of a fluid enclosure. Periodic surface waves are created by coordinating the SMA fiber actuators that move individual points on the surface in both vertical and horizontal directions. This actuator system allows the bedridden to transfer to a chair while lying on the bed as well as transfer between a chair and a toilet without physical effort or external influence. By creating different patterns of coordinated motion, the bed surface can provide various stimuli to the bedridden. An important example is the prevention of bedsores by supporting the body at alternating contact surfaces.

SMA fiber actuators produce large forces in a compact body and can be woven into furniture and textile fabric. SMA fiber actuators may be densely arranged in a water bed to make the bed surface active. Individual points on the bed surface may be connected to multiple fiber actuators so that the point can move up and down vertically as well as slide horizontally. By coordinating the vertical and horizontal motions, a surface wave may be generated which transports the human lying on the bed surface. SMA actuators are generally characterized by a slow speed of response due to low heat dissipation rates. In accordance with an embodiment of the present invention, fiber type SMA actuators are submerged in a water bed to cool the fiber down rapidly. By combining SMA fiber actuators with a water bed, the major drawback of SMA actuators is overcome, and a comfortable sleep surface is obtained as well.

The present invention may reduce or eliminate the need for physical assistance by caretakers in transferring the bedridden between the bed and chair as well as a chair and toilet.

BRIEF DESCRIPTION OF THE DRAWINGS

The foregoing features of the invention will more readily be understood by reference to the following detailed description taken with the accompanying drawings in which.

DETAILED DESCRIPTION OF SPECIFIC EMBODIMENTS

The present invention and its several improvements will be understood when the following detailed description is read in conjunction with the attached drawings. These drawings are intended to provide a better understanding of the present invention, but they are in no way intended to limit the scope of the invention.

Figure 1:
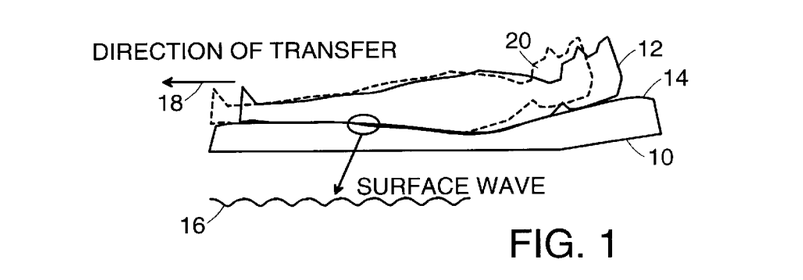
FIG. 1 is side view of a bed showing the position of a prone subject prior to and following translation by a surface wave in accordance with an embodiment of the present invention.

Referring to FIG. 1, a side view is shown of a bed 10 in accordance with a preferred embodiment of the present invention. A subject 12, who will be referred to as a human, without limitation, in this description and in the appended claims, is supported by upper surface 14 of bed 10. It is to be understood that the invention may also be applied for the support and conveyance of other subjects, animate or inanimate, within the scope of the invention and of the appended claims. Surface 14 is textile-like in that it is capable of extension and contraction, and of motion, to some extent, in a direction normal to surface 14 itself. Each segment of surface 14, thus, has three degrees of freedom, allowing motion vertically and in two orthogonal directions in the plane of the surface. The segment, which may be referred to herein as an active unit, may move in coordination with adjacent active units to generate a wave 16 which may have a variety of characteristic motions to be described below. One function of wave 16 is to provide for transfer of subject 12 in a lateral direction 18 to a second and later position 20.

Figure 2:
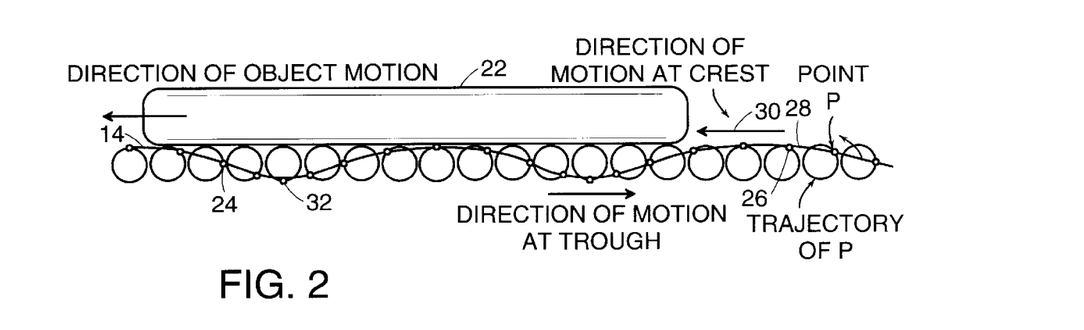
FIG. 2 depicts the principle of surface wave transportation of a subject on a surface in accordance with an embodiment of the present invention.

Transportation of a body 22 is now described with reference to FIG. 2. To transport body 22 lying on surface 14, each active unit moves along a circular trajectory 24 while maintaining a controlled phase difference with respect to motion of each adjacent active unit. At a crest 26 of wave 28, each unit moves at the highest velocity in a horizontal direction 30. As a consequence, body 22 which is supported by the crests moves in the same horizontal direction 30 as the crests. The contact points on the transported body as well as the wavy surface change continually. It is to be noted that troughs 32 of the wave are detached from body 22 and move so that each active unit can return to its original position and repeat the cycle. While the average position of each active unit is stationary, the body is transported horizontally.

In addition to transporting the entire body 22 lying on surface 14, it is often desirable to change the posture of the body. To that end, surface waves may be generated locally over a particular area supporting a body part or limb which is to be relocated relative to the surface. Since each active unit moves independently, local waves may be created to move various body parts in a unique manner at specified individual contact surfaces.

For example, to prevent bedsores, the area supporting the body of a person may be altered by generating a wavy surface and altering the spatial location of its crests and troughs over time. The same technique may additionally be advantageously employed for massaging the body.

One means of creating the wave motion of surface 14 as described above is through the use of electromechanical drives known to persons skilled in the mechanical arts. For example, a series of mechanical nodes may be coordinated to generate an overall surface wave behavior. Matching pairs of mechanical nodes may be connected by bars and driven in tandem in a coordinated manner, as by a motor driven slider-crank mechanism or other means known in the mechanical arts. Using a slider-crank mechanism, the shape of the nodal trajectory may be adjusted. By adjusting the length of the radius of the crank, the vertical displacement of the node and thus the amplitude of the resultant surface waveform may be adjusted. By adjusting the position of the connecting rod with respect to the bar, the horizontal displacement of the node may be adjusted.

Since an application of the present invention is the support of bedridden patients, it is desirable that the contact surface with the subject provide a comfortable environment for sleep and rest. In accordance with a preferred embodiment of the invention, surface 14 which supports the subject may be the upper surface of an enclosure containing a fluid, such as water, for example. The fluid may be a liquid or a gas. Thus, the fluid enclosure may be a modified water bed, thereby combining various favorable attributes of a fluid enclosure, as discussed herein, with the functionality of surface wave actuators. Additionally, a mattress with individually wrapped coil spring actuators may be used to support patients.

Figure 3:
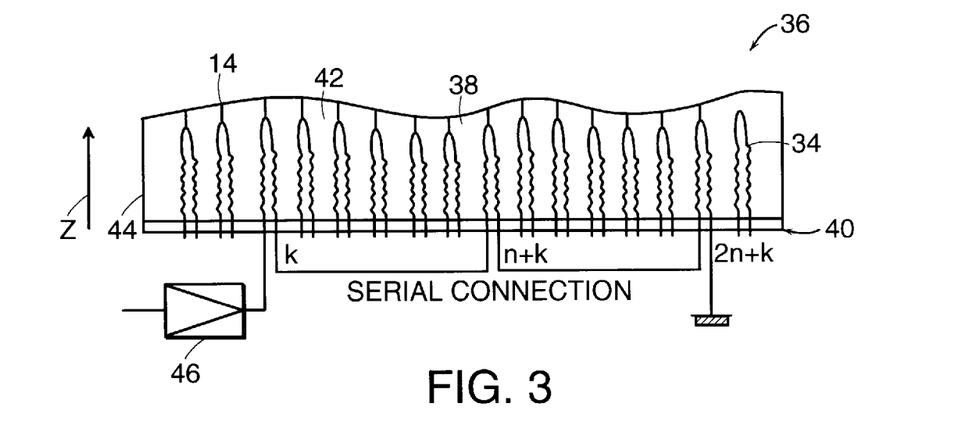
FIG. 3 is a schematic side view of an embodiment of the present invention employing vertically disposed shape memory alloy actuators.

Referring now to FIG. 3, actuation of the support surface of the fluid enclosure may be provided by fiber actuators 34 which may be composed of a shape memory alloy such as NiTi or other contractile material. Work may be extracted from the class of shape memory alloys which includes the nickel/titanium alloy sold as Nitinol, as well as other metallic alloys such as InTl, CuZn, NiAl, AgZn, AgCd, and others. Numerous shape-memory alloys are discussed in H. Funakubo (ed.), *Shape Memory Alloys*, (Gordon and Breach, 1987), which is incorporated herein by reference. Common to these materials is the large change in Young's modulus as each material undergoes a martensitic phase transition from a martensitic phase (at lower temperature) to austenite (at higher temperature). If the material undergoes elongation on heating under compression, or contraction on cooling under tension, mechanical work is provided. By virtue of the hysteresis in the temperature-strain curve, more work may be extracted on heating than returned on cooling. It is known that strain may be applied to shape memory alloys, and work may derived therefrom, in tension, compression, torsion, flexion, etc.

Shape memory materials are currently used in a plethora of applications from heat engines to artificial hearts, as discussed in V. Varadan (ed.), *Smart Structures and Materials: Smart Materials*, Proc. SPIE 2189 (1994), which is herein incorporated by reference. A further useful application of shape memory materials is taught in the present invention.

NiTi SMA actuators may be actuated simply by applying an electrical current through the fiber so as to heat the fiber. Submerging SMA fiber actuators in the fluid enclosure may greatly enhance the heat dissipation characteristics of the fibers and thereby dramatically improve their response speed. Additionally, the ambient temperature of the SMA actuators is readily controlled by regulating the temperature of the fluid using conventional means.

Referring further to FIG. 3, a configuration of fiber actuators is shown by way of example, in accordance with a preferred embodiment of the invention, whereas many configurations may be realized within the scope of the invention. In the configuration shown in FIG. 3, actuators 34, which may be SMA fiber actuators, are disposed in a direction normal to surface 14, this direction denoted as the z axis. In the case of a bed, designated generally by numeral 36, the normal direction is vertical. Volume 38 between wavy bed surface 34 and base plate 40 is filled with a fluid 42 which is typically water but may also be air. Fluid 42 is contained within enclosure 44. Actuators 34 are submerged in fluid 42. Since enclosure 44 is pressurized by virtue of fluid 42 contained within it, SMA fiber actuators 34 are pulled upwards and do not slack. When individual fiber actuators 34 are heated, tensile forces are produced, and the bed surface deforms.

If each fiber is driven by an independent power amplifier 46, numerous amplifiers are required. In accordance with an embodiment of the invention, those fiber actuators 34, here numbered 1 through N, which are in identical phase over successive waves, may be driven by the same power amplifier 46. Thus, if one complete period is completed over n actuators, every n-th actuator is in phase, and the k-th, (n+k)th and (2n+k)th actuators may be driven by the same amplifier. Since NiTi SMA fiber typically exhibits low electrical resistance, series connection of corresponding fibers in typically preferred.

Figure 4:
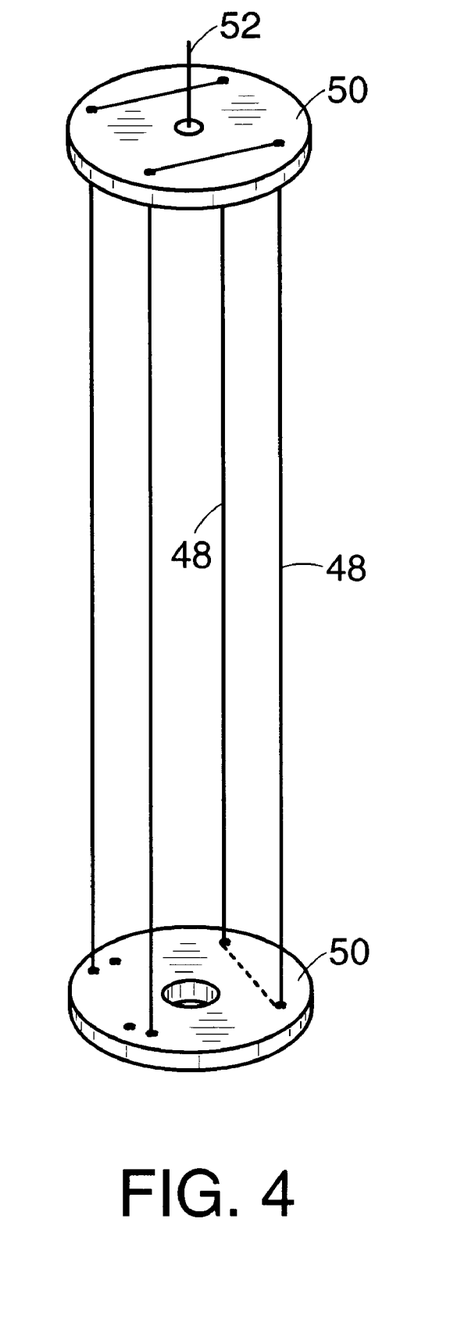
FIG. 4 is a perspective view of an arrangement of shape memory alloy fibers to form a linear actuator in accordance with an embodiment of the invention.

Referring now to FIG. 4, an arrangement of SMA fibers 48 into a linear actuator is shown in perspective. Each fiber is typically cylindrical and on the order of 6–8 thousandths of an inch in diameter. Such fibers may produce forces on the order of 5–10 Newtons for lengths typically employed. Because of their small size, fibers 48 may be woven tightly throughout the bed. To produce large forces, wires 48 are woven in parallel, but are connected electrically in series by wrapping the wires about insulators 50 as shown. This causes the forces to add constructively. A substantially non-extensible cable 52 connects one end of actuator 34 to a node of the upper surface of the enclosure.

Figure 5:
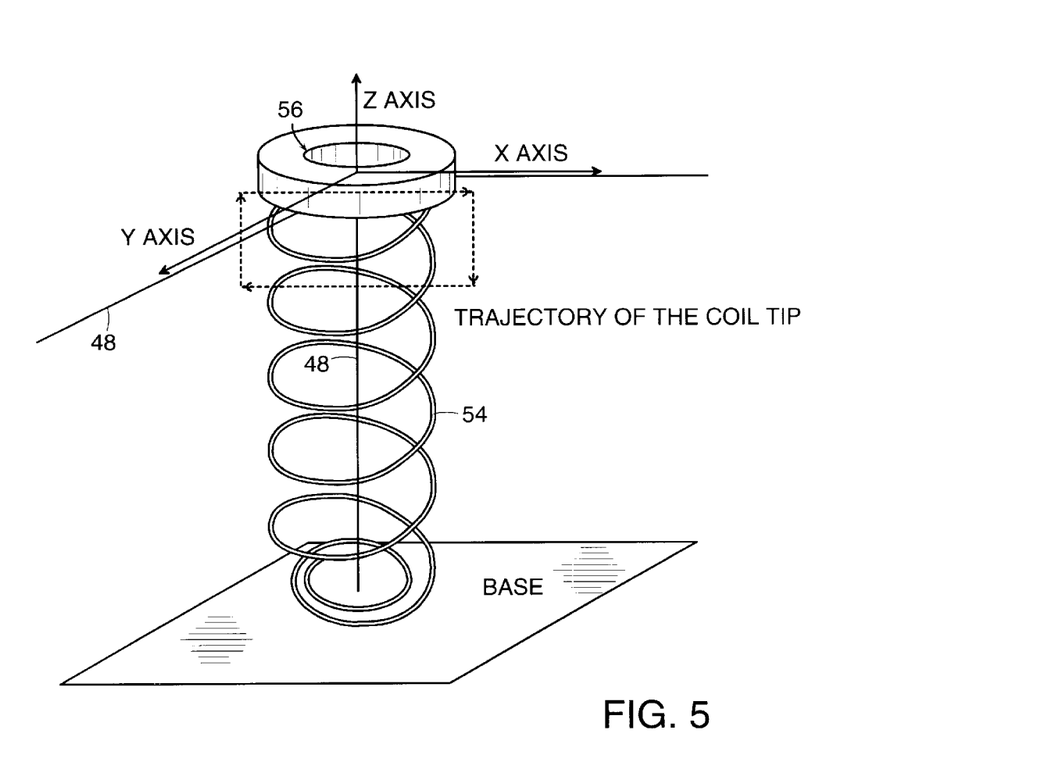
FIG. 5 shows an SMA fiber actuator employed in conjunction with a coil spring in accordance with an embodiment of the invention.

Referring now to FIG. 5, each actuator node is connected to a mattress coil spring 54 in order to apply tension in the vertical (z) direction, as well as along lateral (x and y) directions for providing lateral motion. Shape memory fibers 48 may apply forces in each direction, as may lateral cables, such as steel cables, traveling over pulley rods mounted at the ends of the bed and pulled by motors. Contact pressure sensors 56 may be disposed at some or all of the nodes in order to provide feedback signals for an active control loop driving the surface wave movements.

Figure 6:
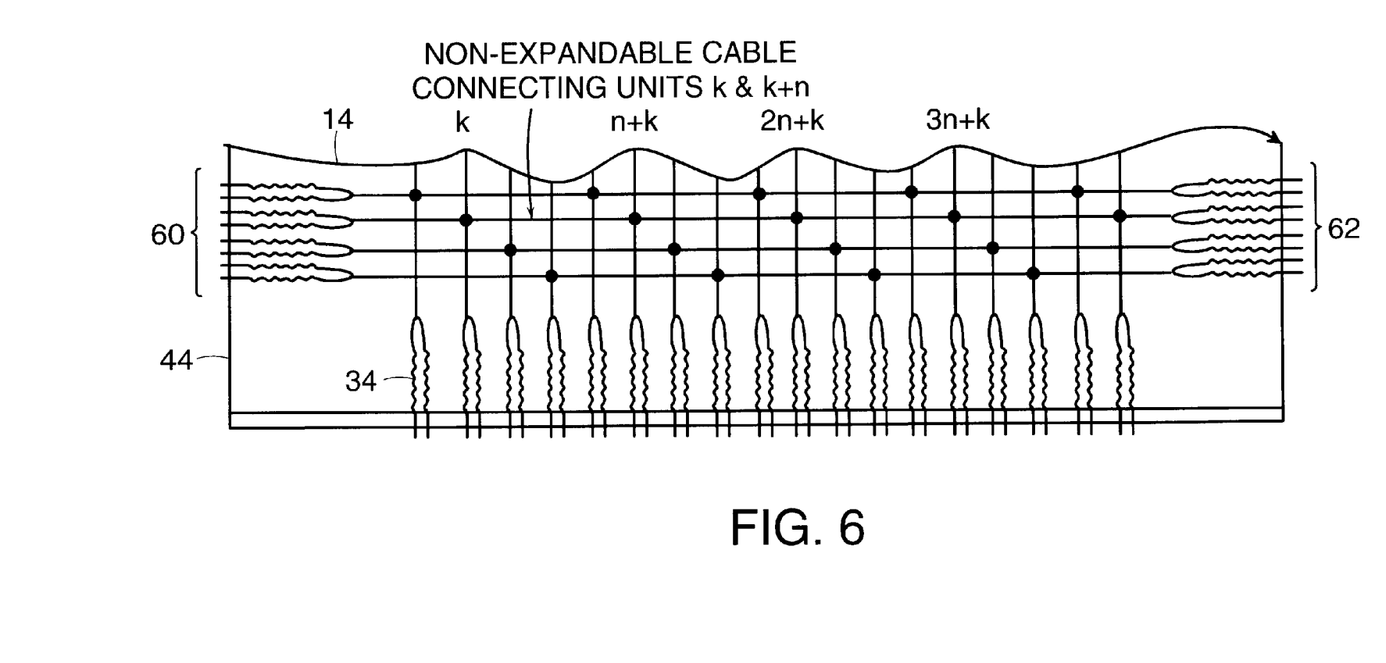
FIG. 6 is a schematic side view of an embodiment of the present invention employing shape memory alloy actuators disposed both vertically and horizontally.
Figure 7:
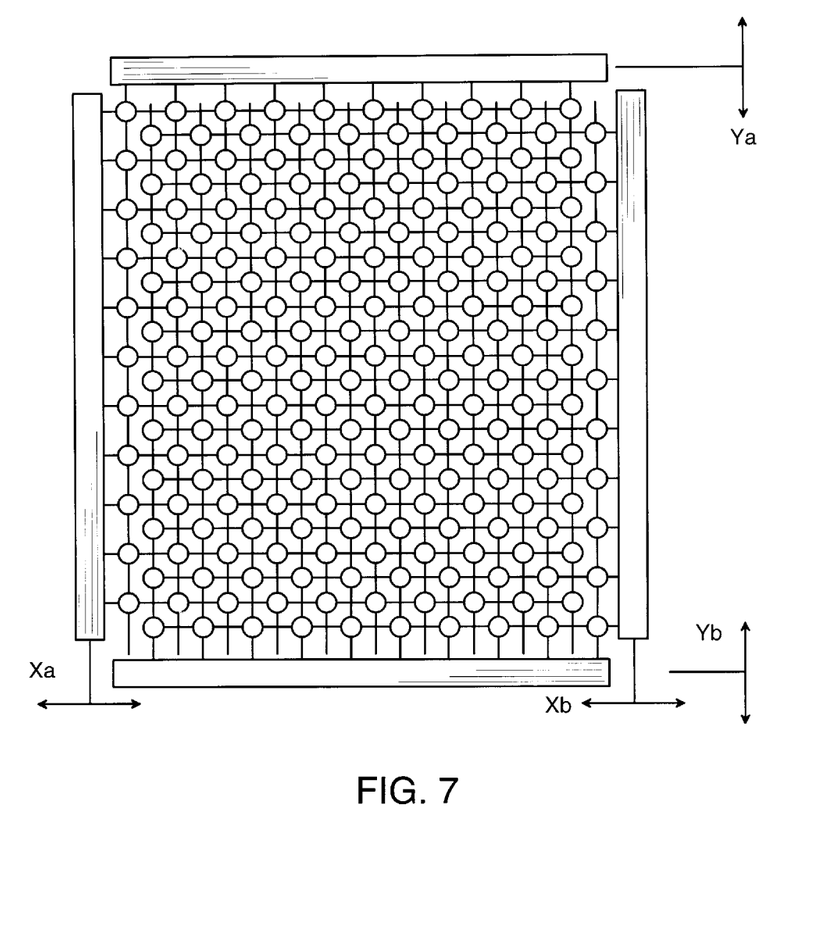
FIG. 7 is a schematic top view of the embodiment of FIG. 6, showing lateral coupling between nodes.
Figure 8:
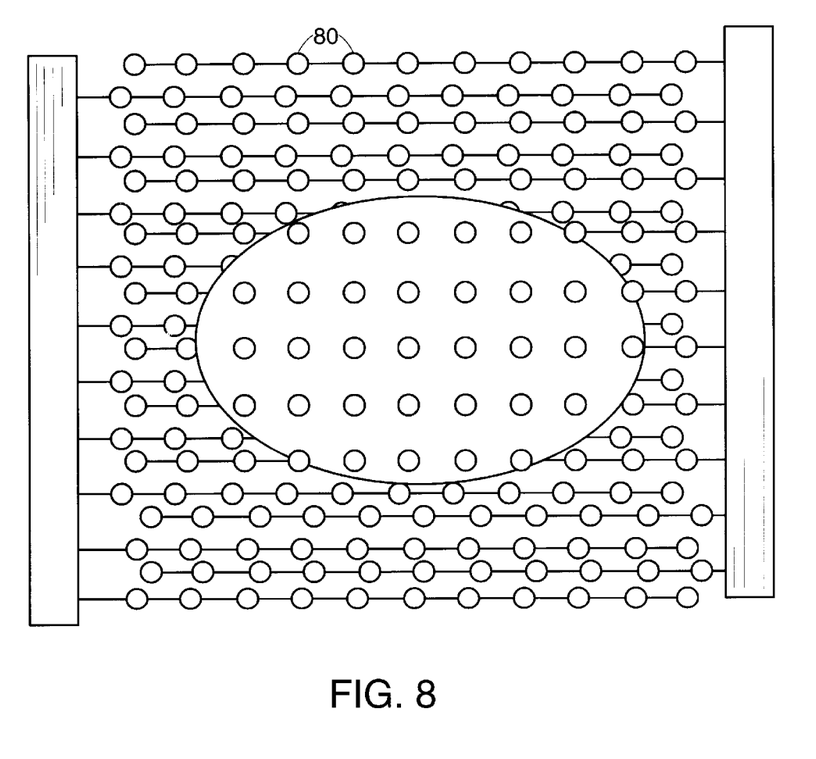
FIG. 8 is a top view, with an expanded inset, showing the shape of active elements subject to the concurrent vertical and lateral activation of the embodiment of FIG. 6.

For horizontal movements, all units moving in phase may be mechanically connected by substantially non-extensible cable, as shown in FIG. 6. Each group of units connected together are pulled horizontally by two sets 60 and 62 of SMA fiber actuators arranged in an antagonistic form on either side of enclosure 44. Vertical actuators 34 act to deform wavy surface 14 as described above. A number n of independent groups of horizontal actuators are coordinated so that the phase difference between adjacent groups is substantially $2\pi/n$, for equally spaced actuators. The orthogonal sets of horizontal actuators in accordance with the design of FIG. 6 are shown in a particular plane in the vertical view of FIG. 7. Referring now to FIG. 8, a top view is shown, with an expanded inset, of the shape of active units 80 subject to the concurrent vertical and lateral activation of the embodiment of FIG. 6.

Figure 9:
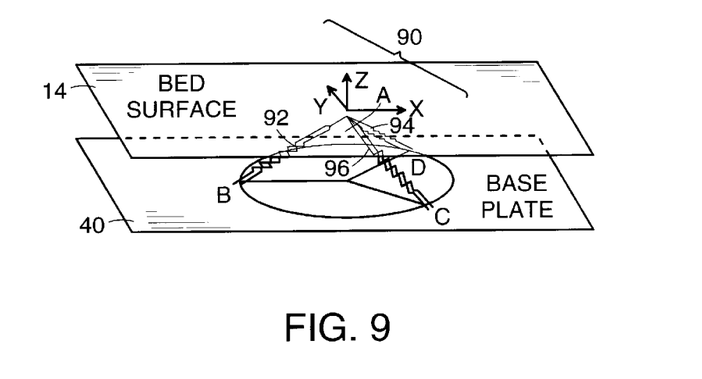
FIG. 9 is a schematic side view of an embodiment of the present invention employing shape memory alloy actuators disposed to control three degrees of freedom.

The embodiment of FIG. 6 may be limited in flexibility, in that the wiring arrangement as well as the mechanical connection are substantially fixed. In order to achieve greater flexibility of application, each active unit may be independently moveable and the electrical drive connections reconfigurable. FIG. 9 shows one independent active units 90 driven by three SMA fiber actuators, 92, 94, and 96. Point A on the bed surface 14 may be pulled down toward three points on the base plate 40. As the three fiber actuators create contraction forces in three oblique directions, the junction A moves in three directions, with the fluid within the bed enclosure providing the bias force pulling point A upward. To generate a wave on surface 14, in accordance with an embodiment of the invention, many units may be grouped together by exploiting wave periodicity. Hard wiring is not appropriate, however, since different waves may require different wiring combinations. To resolve this problem, in accordance with an alternate embodiment of the invention, a programmable electrical connection mechanism using microrelays is employed for this two-dimensional transportation system. Depending on the waveform, wavelength, and propagation direction, different groupings of fiber actuators are formed and each independent group may be connected to a single power amplifier. To generate a different set of waves, a reduced number of power amplifiers may be required.

Figure 10:
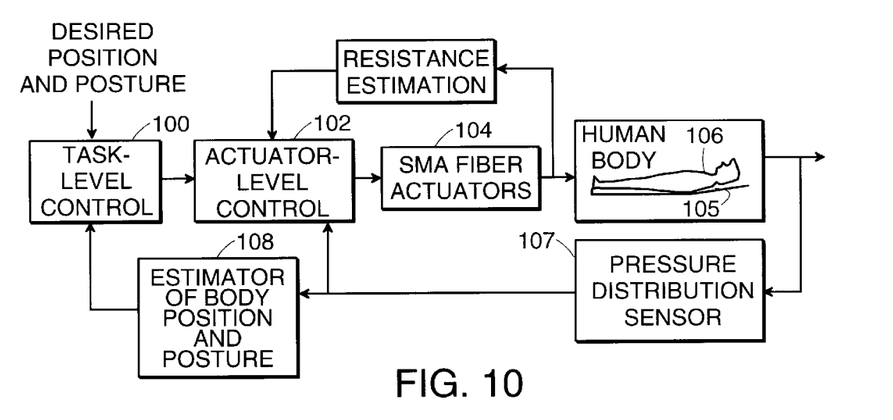
FIG. 10 is a schematic diagram of a closed loop human position control mechanism in accordance with an alternate embodiment of the present invention.

FIG. 10 shows a block diagram for a closed human position/posture control loop. Desired body position and posture are input into the upper task level 100 of the controller. This feeds velocity/position information to the actuator controller 102. This, in turn, commands the XYZ actuators 104 on the bed surface 105 for moving load 106 which may include a human patient. The feedback path may include pressure sensors 107, and, in accordance with a preferred embodiment of the invention, distributed pressure sensors are employed to provide a feedback signal for the task level controller 100 and actuator control 102. This information is used by processor 108 for estimating the position of the human body and its orientation. The information is also used by the actuator controller, to determine velocity and position requirements of the nodes distributed across surface 105.

Transferring to and from a car seat

Figure 11:
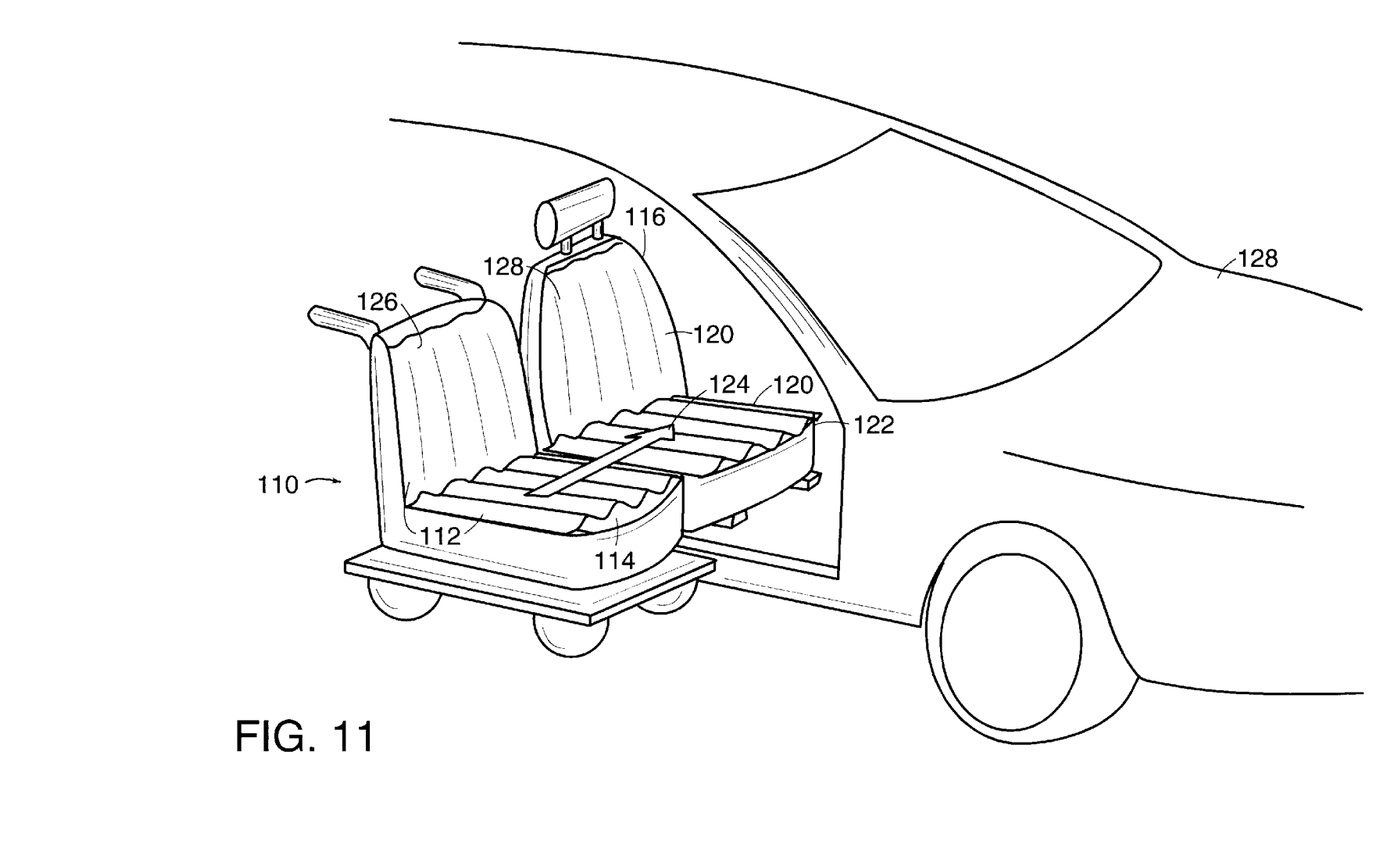
FIG. 11 is a side view of an embodiment of the present invention permitting the transfer of a subject from a wheelchair to a car seat.

A further alternate embodiment of the invention relates to an automobile passenger transfer system described now with reference to FIG. 11. A wheelchair 110 with a surface wave actuator 112 applied to seating surface 114 is docked side-by-side with car seat 116 of automobile 118. Car seat 116 is also equipped with a surface wave actuator 120 applied to seating surface 122. Waves are created, in accordance with the description above, on both car seat 116 and wheelchair 110 so that the passenger may be transferred sideways, in the direction 124 shown in the figure. Waves may also be generated on backs 126 and 128 of the wheelchair and car set, respectively, so that a passenger may be transferred while resting on the back. In order to eliminate a gap between the car seat 116 and the wheelchair 110, car seat 116 may be pulled out from its regular position within the cabin of automobile 118, using mechanisms known to persons of ordinary skill in the mechanical arts. Additionally, a mechanism for varying the height of either the wheelchair or car seat may be provided in accordance with the invention.

By virtue of the car transfer method described, standard sedans may be employed for the transport of handicapped subjects in cases where high-roof cars would otherwise be required. Additionally, the passenger, in accordance with this aspect of the invention, is at all times fully supported from below.

Transferring to and from a bathtub

Figure 12:
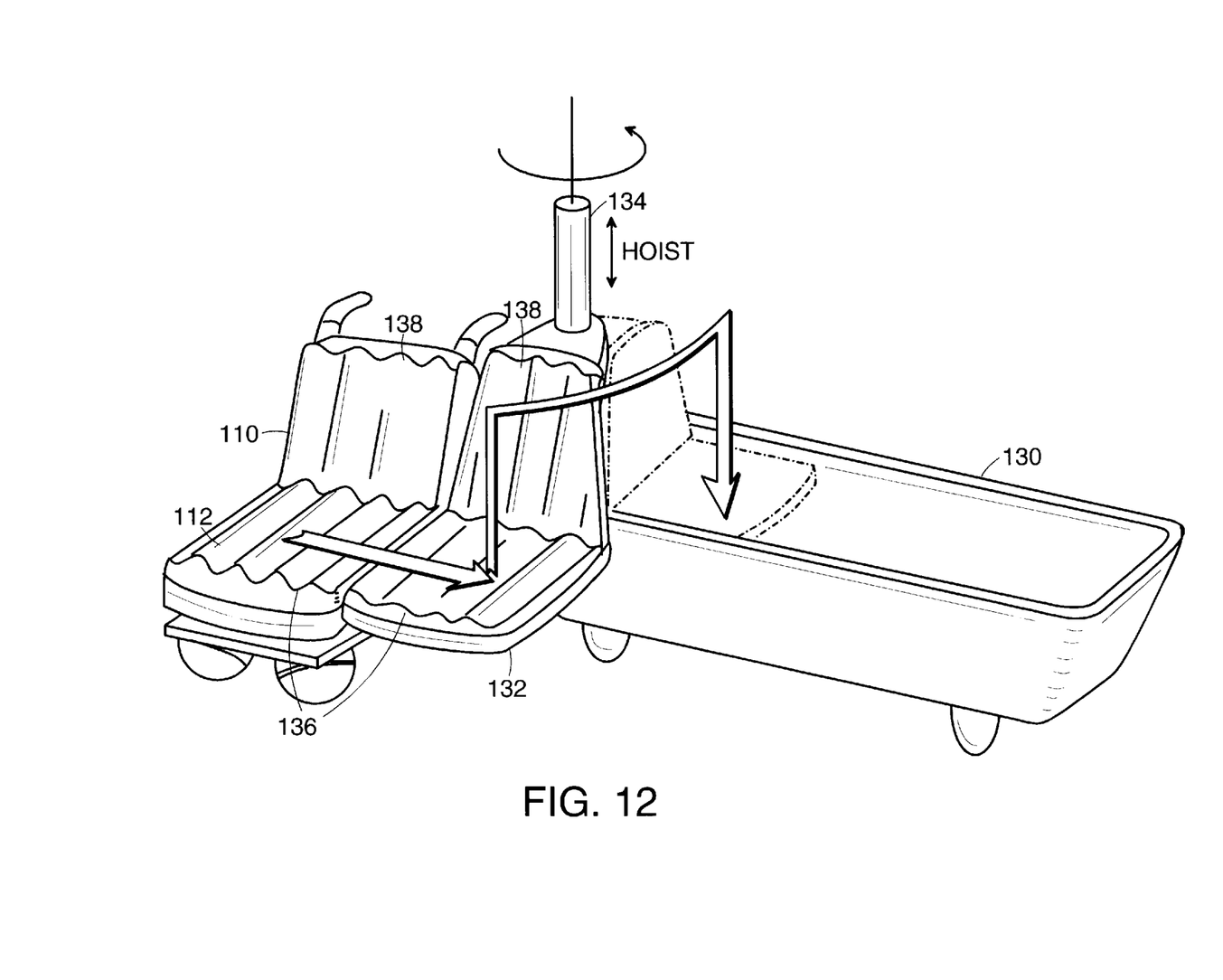
FIG. 12 is a side view of an embodiment of the present invention permitting the transfer of a subject from a wheelchair to a car seat.

FIG. 12 depicts a method of transferring a patient between a wheelchair 110 and a bathtub 130 in accordance with an embodiment of the present invention. The bathtub shown is a standard model which has been used in nursing homes for years, and is shown by way of example. Bathtub 130 is equipped with a chair 132 and a hoist 134 to transfer a patient into the bathtub. As in the transfer to a car seat discussed above, wheelchair 110 is equipped with a surface wave actuator surface 112 and is docked beside chair 132 attached to the bathtub. Surface waves 136 are generated on both the wheelchair and bathtub chair such that the patient may easily slide on both seats and from one to another. Waves may also be generated on the back leaves 138.

Changing Clothes While Seated

Figure 13:
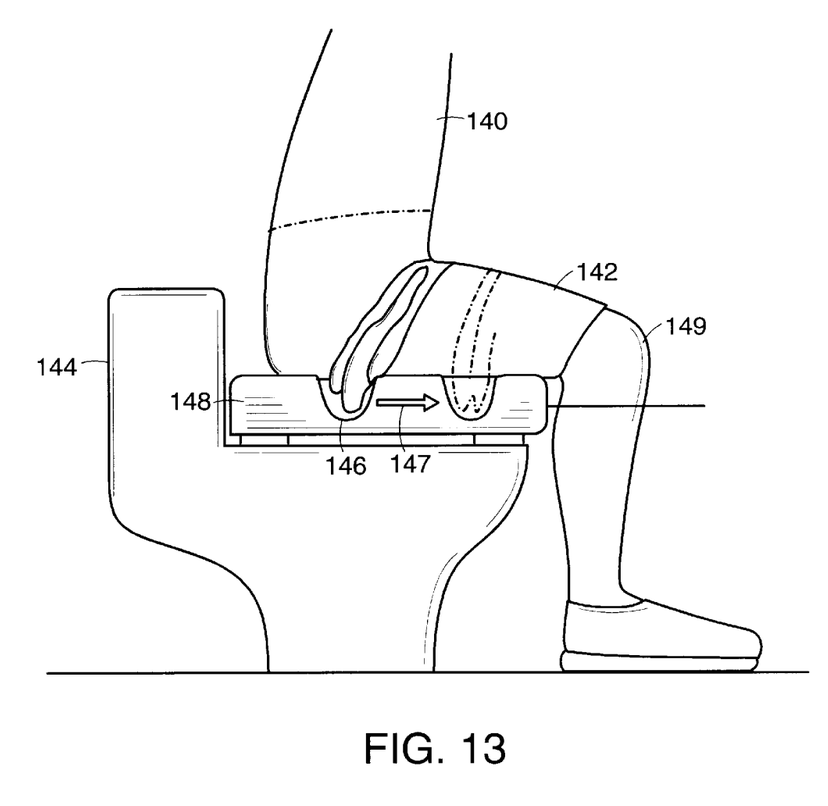
FIG. 13 is a side view of an embodiment of the present invention permitting a patient to remove underwear while seated.

In accordance with a further alternate embodiment of the invention, surface wave actuators may be employed for assisting persons such as handicapped or bedridden patients to change clothes. FIG. 13 shows a patient 140 removing his/her underwear 142 while seated on a toilet 144. A u-shaped groove 146 or pocket is created by a surface wave actuator embedded in toilet seat 148. As underwear 142 is removed toward legs 149, the position of pocket 146 is moved in the same direction 147. In other words, the groove, i.e., a single wave, propagates through toilet seat 148 so that the underwear can be removed from the waist while the patient is sitting on the toilet.

The same technique may be applied to changing sheets and clothes for bedridden patients. Changing a sheet, for example, can be performed without moving the patient in the bed. By tucking a sheet into a deep groove created on the bed surface, the sheet may be stretched or folded beneath the patient's body as the patient is lying on the bed. The patient's body is supported at all times by parts of the bed other than the contemporaneously recessed groove. The movement of the groove is coordinated with the stretching or folding motion of the sheet.

Fine Positioning of a Subject for MRI and X-Ray Scans

Figure 14:
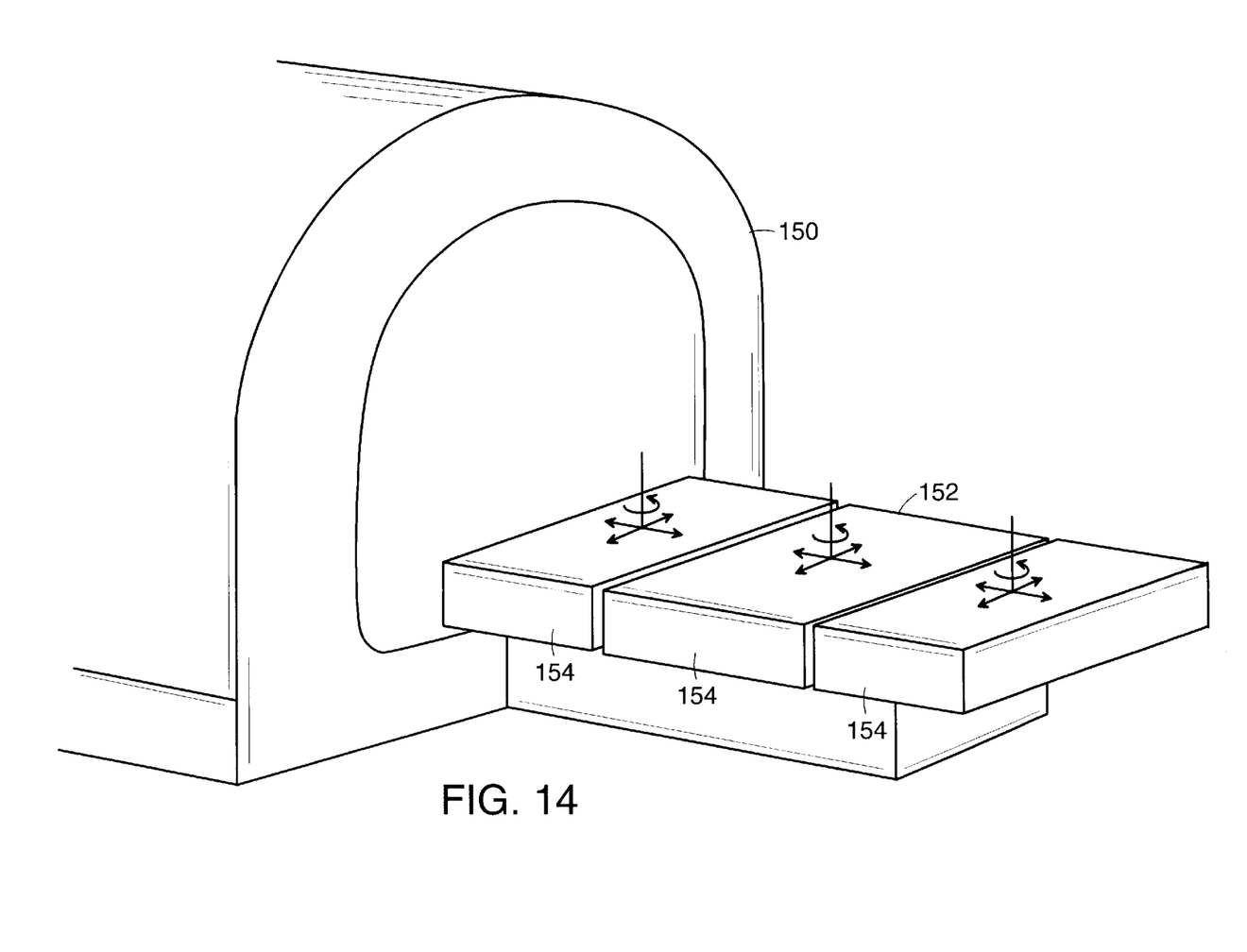
FIG. 14 is a side view of an embodiment of the present invention permitting the positioning of a subject for a medical procedure or exam.

Proper positioning is often important in obtaining useful data in magnetic resonance imaging (MRI) and x-ray examinations as well as in other medical examinations. Surface wave actuators may be employed, in accordance with an embodiment of the invention, for the fine positioning of patient bodies in various medical equipment. FIG. 14 shows MRI system 150, including a bed 152 comprised of segments 154 equipped with surface wave actuators. The patient posture may be modified by creating surface waves at specified locations on the bed surface where the patient body must be moved. The patient posture is measured, for example, by pressure sensors distributed within or on the bed surface, and closed-loop control may be formed for driving the patient body to a desired configuration.

While the invention has been described in detail, it is to be clearly understood that the same is by way of illustration and example and is not to be taken by way of limitation. Indeed, numerous variations and modifications will be apparent to those skilled in the art. All such variations and modifications are intended to be within the scope of the present invention as defined in the appended claims.

We claim:

1. An apparatus for supporting a human subject, the apparatus comprising:
   a. a fluid enclosure containing a fluid and having a top surface;
   b. an actuator mechanism including a plurality of linear actuators enclosed entirely within the fluid enclosure for causing local deformations of the top surface of the fluid enclosure in such a manner as to create traveling waves whereby a force tangential to the top surface is exerted on the subject.

2. An apparatus according to claim 1, wherein the actuator mechanism includes a motor driver coupled to the top surface of the fluid enclosure.

3. An apparatus according to claim 1, wherein the actuator mechanism includes a plurality of linear actuators configured so as to cause local deformations of the top surface in a direction having a vertical component.

4. An apparatus according to claim 3, wherein the plurality of linear actuators include shape memory fibers.

5. An apparatus according to claim 3, additionally including a plurality of fiber actuators configured to cause lateral deformations of the top surface of the fluid enclosure.

6. An apparatus according to claim 5, wherein the plurality of fiber actuators configured to cause lateral deformations of the top surface of the fluid enclosure are woven into the top surface of the fluid enclosure.

7. An apparatus according to claim 1, wherein the apparatus is a bed.

8. An apparatus according to claim 1, wherein the apparatus is a chair.

9. An apparatus according to claim 1, wherein the apparatus is a medical examining table.

10. An apparatus according to claim 1, wherein the apparatus is a car seat.

11. An apparatus according to claim 1, wherein the fluid is water.

12. A method for transferring a human subject from a first surface to a second surface, the method comprising:
 a. positioning the first and second surfaces in substantial adjacency and at substantially equal height;
 b. causing local deformations of the first surface in a direction having a vertical component by means of linear actuators enclosed entirely within the first surface; and
 c. coordinating the local deformations of the first surface in such a manner as to create traveling waves whereby a force tangential to the first surface is exerted on the subject thereby urging the subject onto the second surface.

13. A method according to claim 12, wherein at least one of the first and second surfaces is a chair.

14. A method for transferring a human subject from a surface to a bathtub having a bathtub hoist seat, the method comprising:
 a. docking the surface in substantial adjacency and at substantially equal height to the bathtub hoist seat;
 b. causing local deformations of the surface in a direction having a vertical component; and
 c. coordinating the local deformations of the surface in such a manner as to create traveling waves whereby a force tangential to the surface is exerted on the subject thereby urging the subject onto the bathtub hoist seat;
 d. lowering the subject into the bathtub by means of the bathtub hoist seat.

15. A method of repositioning apparel of a human subject prone or recumbent on a fluid enclosure containing a fluid and having a top surface, the method comprising:
 a. causing local deformations of the top surface of the fluid enclosure in a direction having a vertical component such as to support the subject other than through an unsupported portion of the apparel and other than through a groove wherein the surface does not contact the subject; and
 b. tucking the portion of the apparel away from the subject into the groove.

16. A method for positioning a human subject on a surface, the method comprising:
 a. causing local deformations of the surface in a direction having a vertical component by means of linear actuators enclosed entirely within the first surface such as to support the subject in specified locations; and
 b. coordinating the local deformations of the surface in such a manner as to create traveling waves whereby a force tangential to the surface is exerted on the subject thereby urging the subject into a specified position.

* * * * *